United States Patent [19]

Belko

[11] Patent Number: 5,693,828

[45] Date of Patent: Dec. 2, 1997

[54] PROCESS FOR PREPARING LACTONES AND INTERMEDIATES THEREFOR

[75] Inventor: Robert P. Belko, Woodbridge, N.J.

[73] Assignee: International Flavors & Fragrances Inc., New York, N.Y.

[21] Appl. No.: 647,248

[22] Filed: May 9, 1996

[51] Int. Cl.$^6$ .............................................. C07D 313/00
[52] U.S. Cl. ..................... 549/266; 549/323; 562/577; 562/579
[58] Field of Search ........................ 560/577, 579; 549/323, 204, 266

[56] References Cited

U.S. PATENT DOCUMENTS

| | | | |
|---|---|---|---|
| 2,936,310 | 5/1960 | Beets et al. | 260/340.2 |
| 4,892,955 | 1/1990 | Wada et al. | 549/325 |
| 5,021,589 | 6/1991 | Wada et al. | 549/325 |
| 5,023,351 | 6/1991 | Yoshida et al. | 549/321 |
| 5,099,036 | 3/1992 | Yoshida et al. | 549/321 |
| 5,350,868 | 9/1994 | Yoshida et al. | 554/154 |
| 5,380,912 | 1/1995 | Yoshida et al. | 558/440 |

FOREIGN PATENT DOCUMENTS

| | | | |
|---|---|---|---|
| 229087 | 4/1986 | Czechoslovakia. | |
| 402063 | 12/1990 | European Pat. Off. | C07D 307/33 |
| 95078054 | 4/1987 | Japan | C07D 307/33 |
| 95078055 | 2/1988 | Japan | C07D 307/33 |
| 0311036 | 1/1991 | Japan | C07C 59/215 |
| 9524371A | 3/1994 | WIPO | C07C 29/149 |

OTHER PUBLICATIONS

Ohloff, "Scent & Fragrances", pp. 199–213 (1995).

*Primary Examiner*—James H. Reamer
*Attorney, Agent, or Firm*—Arthur L. Liberman

[57] ABSTRACT

Described is a process for preparing cyclopentadecanolide defined according to the structure:

using as a starting material the dicarboxylic acid having the structure:

according to the reaction sequence:

Also described is a process for using the resultant cyclopentadecanolide for augmenting, enhancing or imparting aromas in or to perfume compositions, colognes and perfumed articles including but not limited to solid or liquid anionic, cationic, nonionic or zwitterionic detergents, perfumed polymers, fabric softener compositions, fabric softener articles, cosmetic powders and hair preparations.

6 Claims, 9 Drawing Sheets

GLC PROFILE FOR EXAMPLE I.

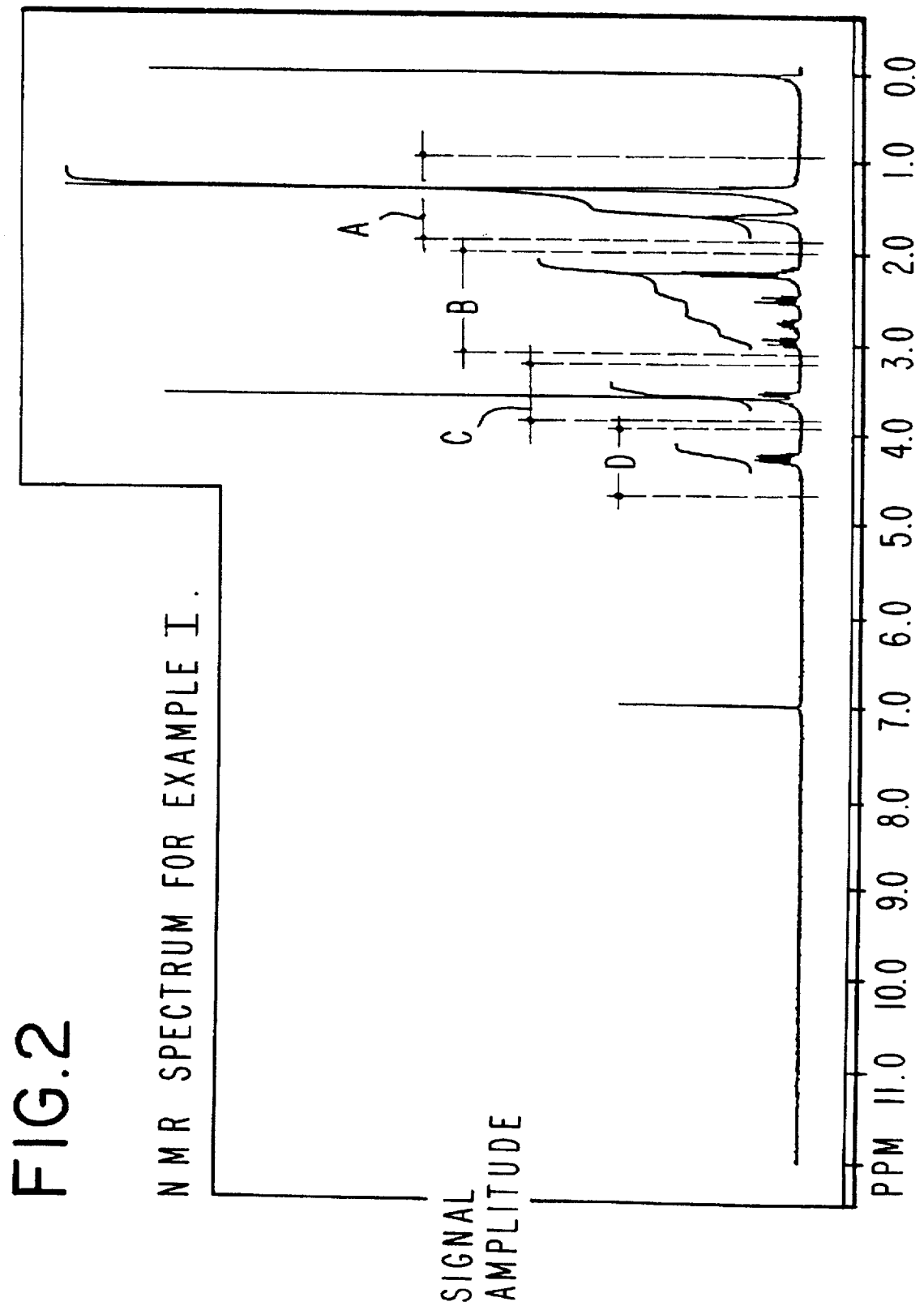
FIG.2 NMR SPECTRUM FOR EXAMPLE I.

FIG.2-A
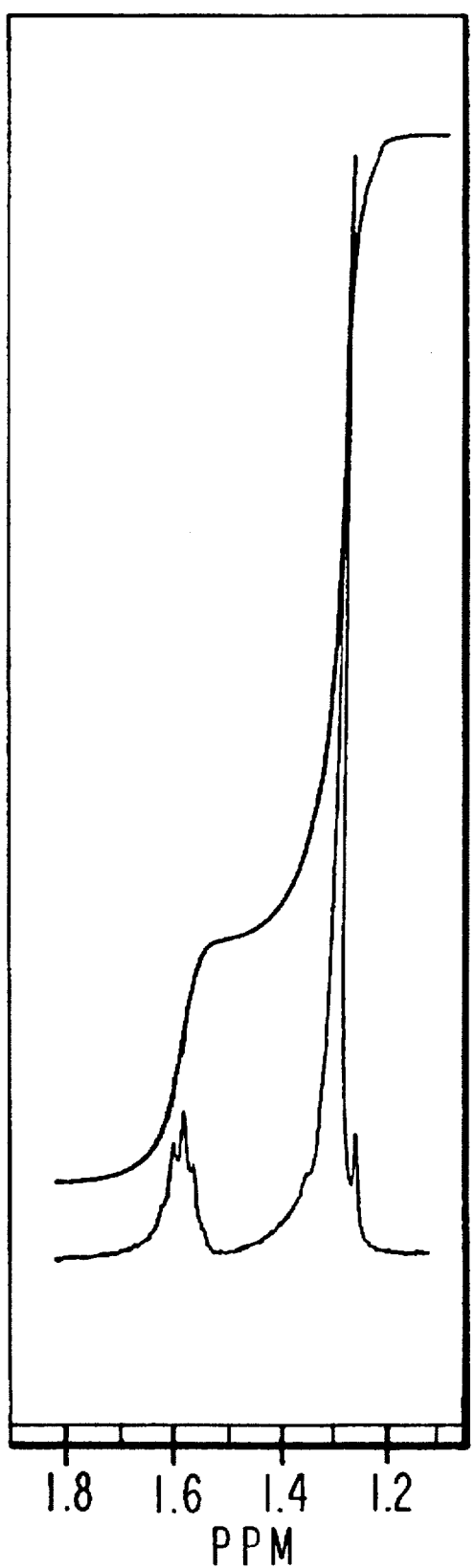

FIG. 2-B
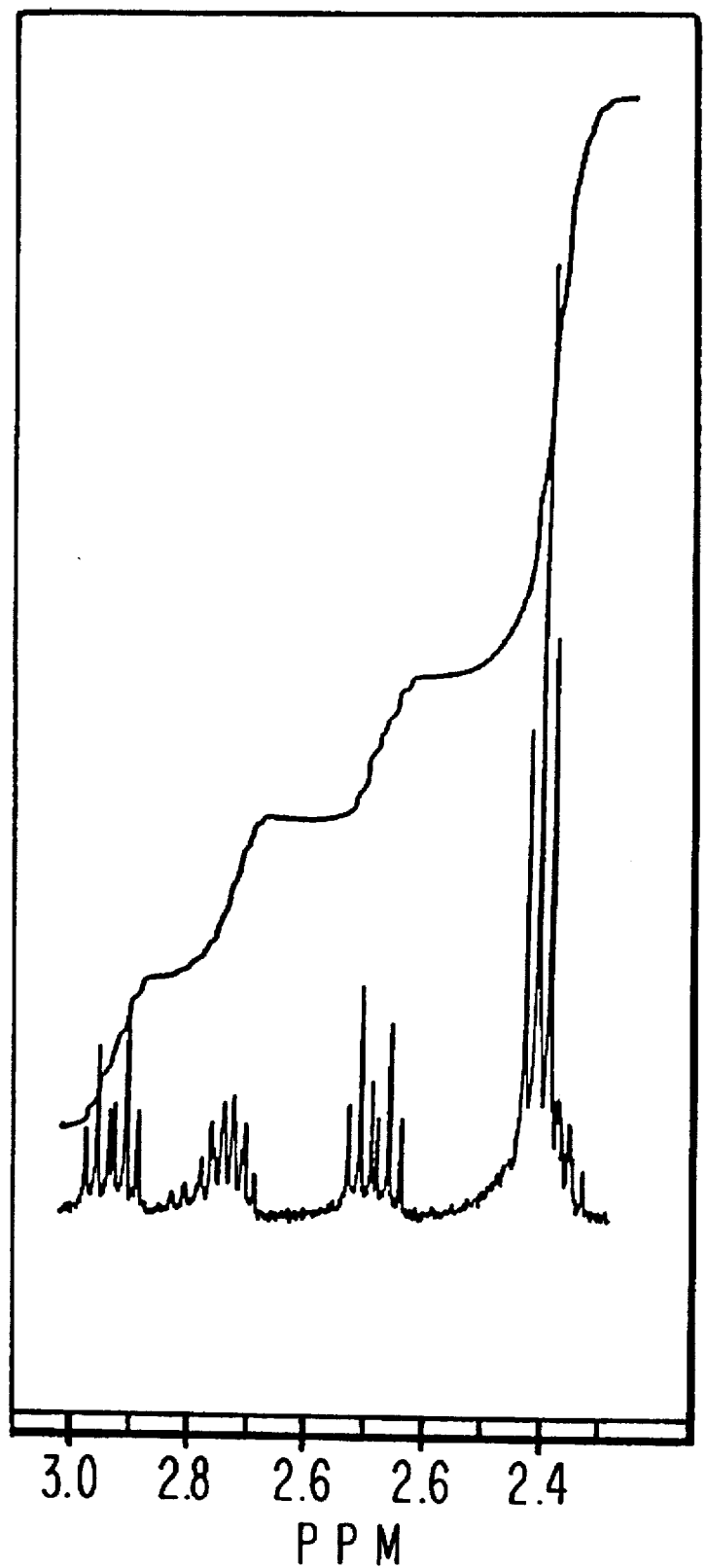

FIG.2-D
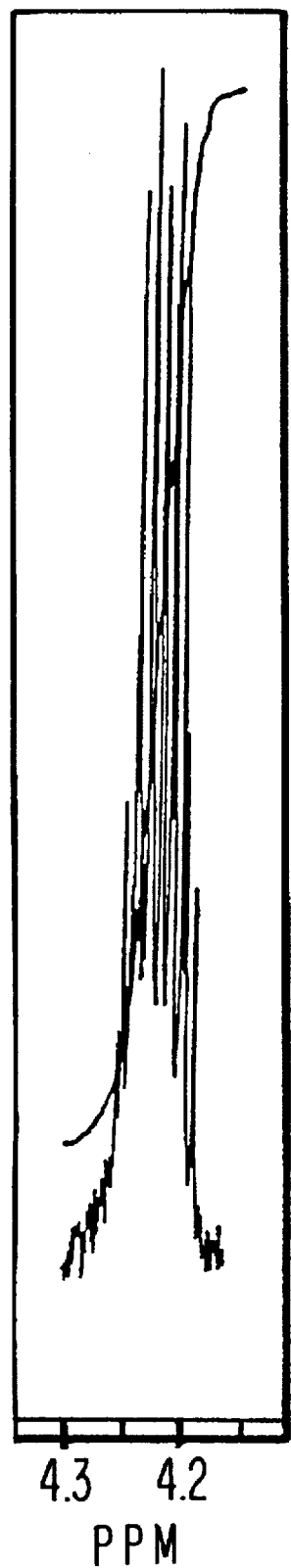
4.3  4.2
PPM
FIG.2-C
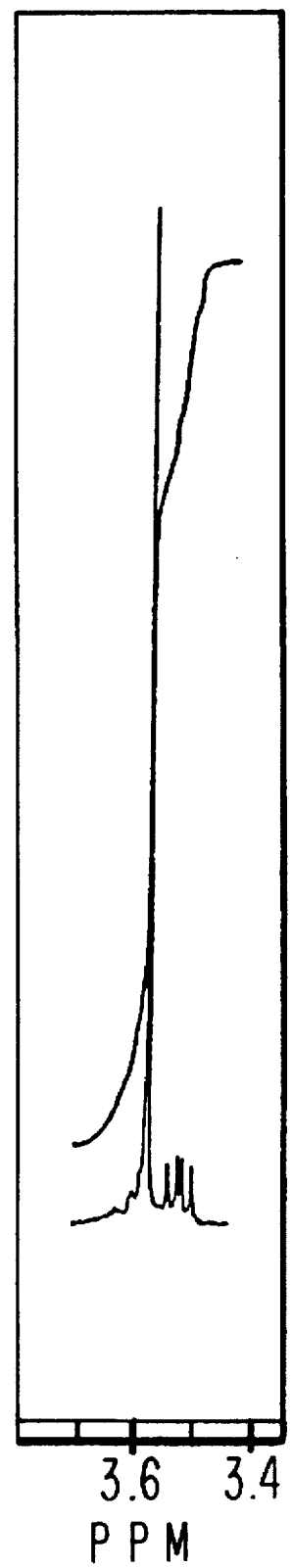
3.6  3.4
PPM

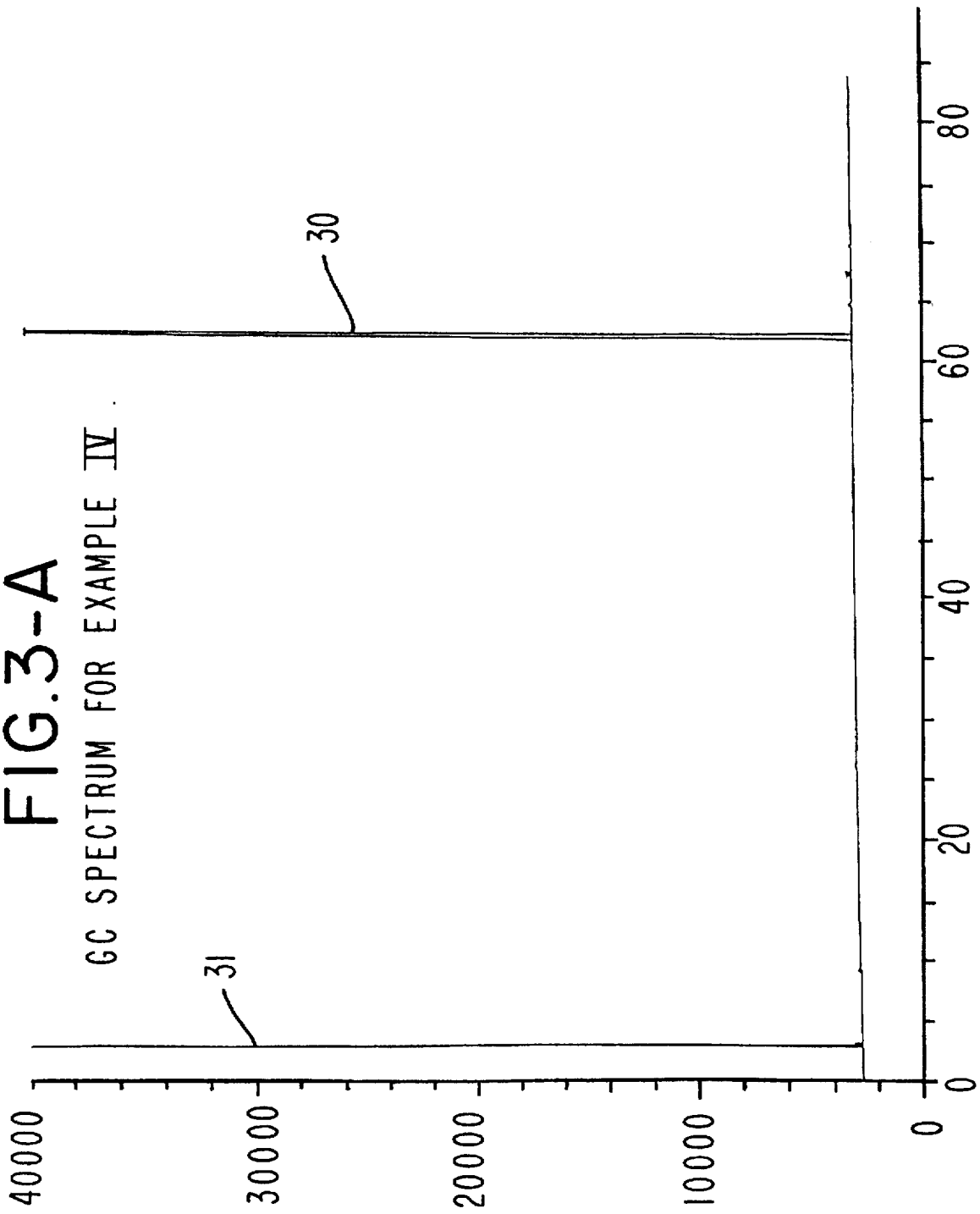

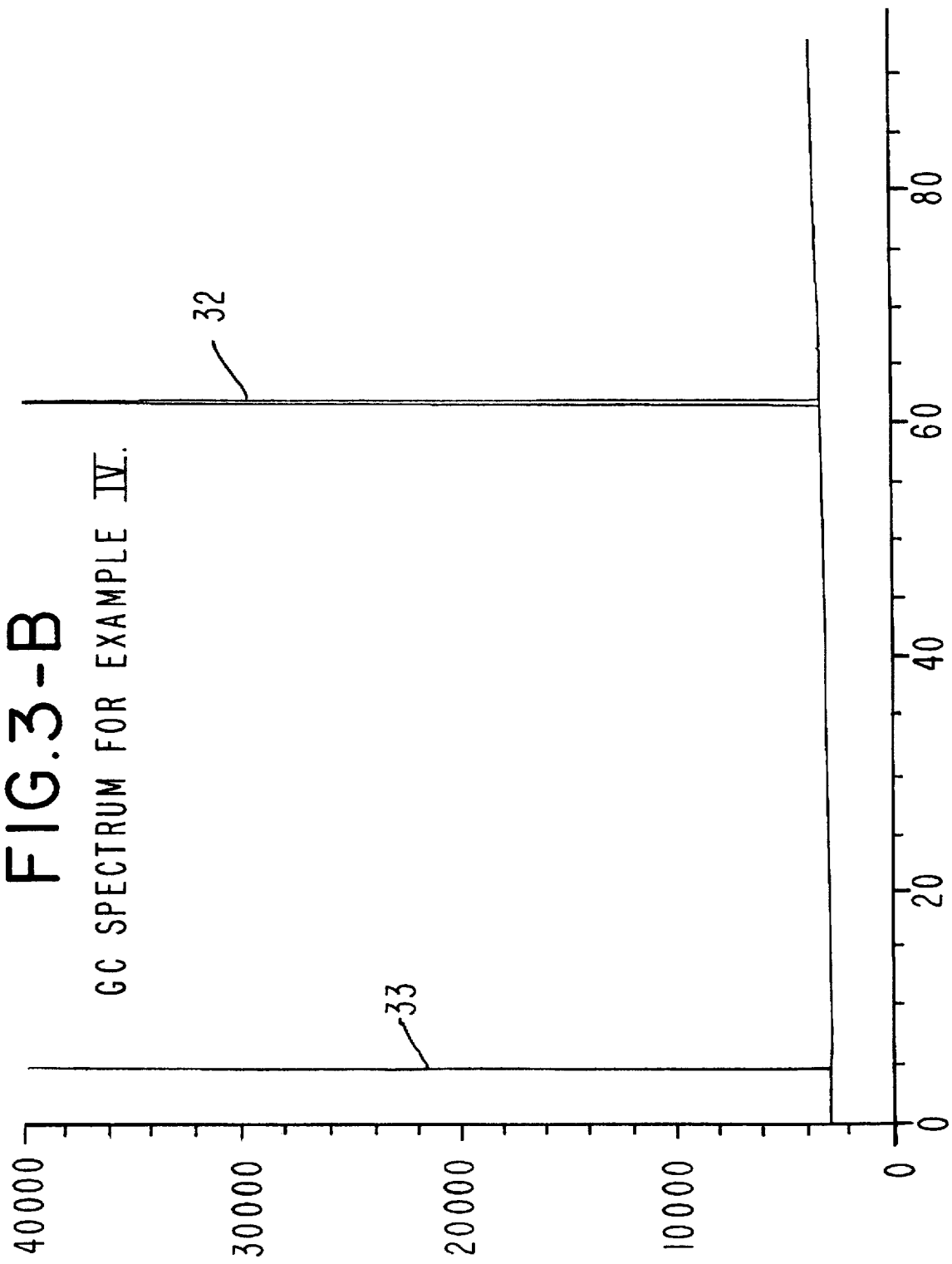
FIG.3-B
GC SPECTRUM FOR EXAMPLE IV.

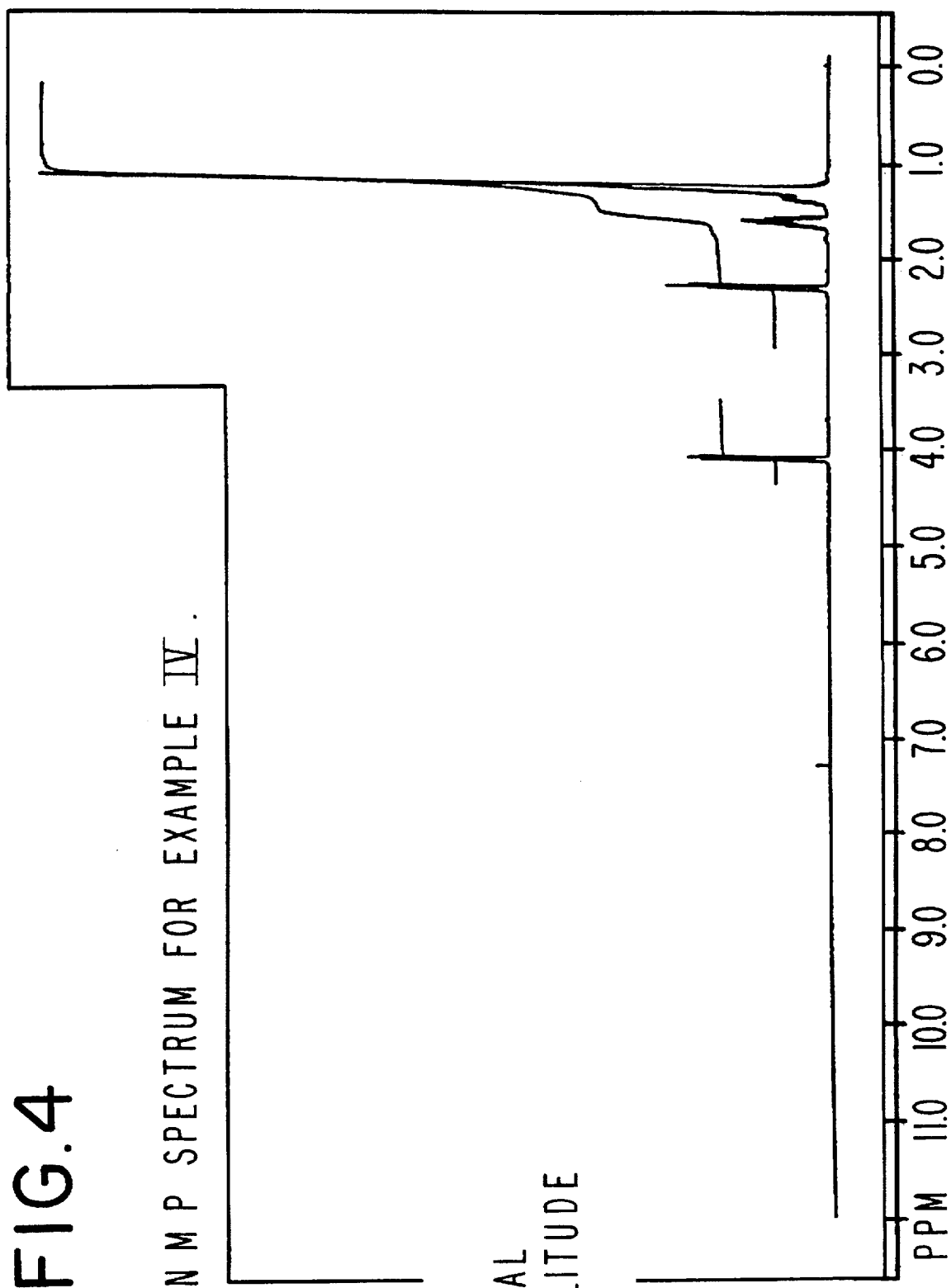

PROCESS FOR PREPARING LACTONES AND INTERMEDIATES THEREFOR

BACKGROUND OF THE INVENTION

My invention relates to a novel process for preparing cyclopentadecanolide having the structure:

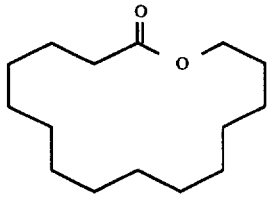

using as a starting material the dicarboxylic acid having the structure:

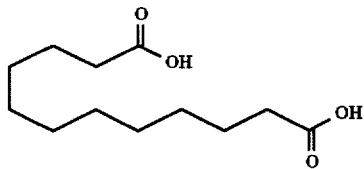

to form the intermediate having the structure:

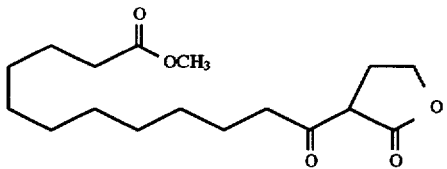

and then using that intermediate having the structure:

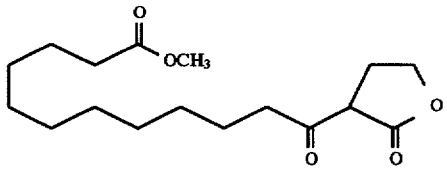

to form the intermediate to form the structure:

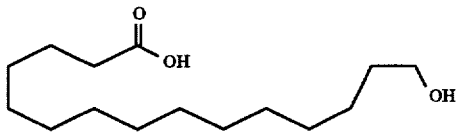

and then cyclizing the compound having the structure:

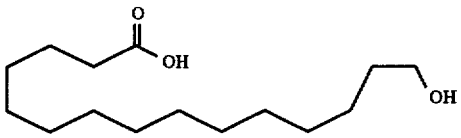

to form the cyclopentadecanolide having the structure:

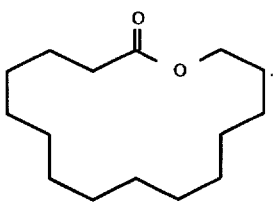

There has been considerable work performed relating to substances which can be used to impart (alter, modify or enhance) fragrances to (or in) various consumable materials. These substances are used to diminish the use of natural materials some of which may be in short supply and to provide more uniform properties in the finished product. Musky aromas are highly desirable in several types of perfume compositions and for use in perfumed articles. Natural "musky" aromas are highly sought after and heretofore have been virtually impossible to duplicate. Accordingly, a need exists in perfume art to duplicate as closely as possible natural musky aroma nuances.

Cyclopentadecanolide having the structure:

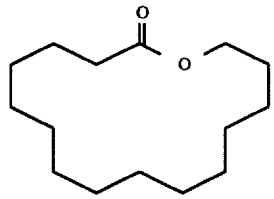

is well known in the art of perfumery giving delicate animal, musky and sweet, extremely tenacious aromas of outstanding uniformity. Furthermore, the cyclopentadecanolide has a fixative and mellowing effect at very low concentrations of usage. This is particularly conspicuous when the fragrance containing the cyclopentadecanolide is applied to the skin, for example, during a washing procedure. Furthermore, such cyclopentadecanolide gives highly interesting effects when applied to certain flavors, for example, those used in alcoholic beverages, dentifrice flavors and the like. The use of the cyclopentadecanolide produced according to the process of my invention is disclosed by Arctander "Perfume And Flavor Chemicals" (AROMA CHEMICALS), Volume I, published in 1969 at monograph 811.

The prior art, including U.S. Pat No. 5,023,351 issued on Jun. 11, 1991; U.S. Pat. No. 5,099,036 issued on Mar. 24, 1992; U.S. Pat. No. 5,380,912 issued on Jan. 10, 1995; and U.S. Pat. No. 5,350,868 issued on Sep. 27, 1994, discloses the reaction sequence:

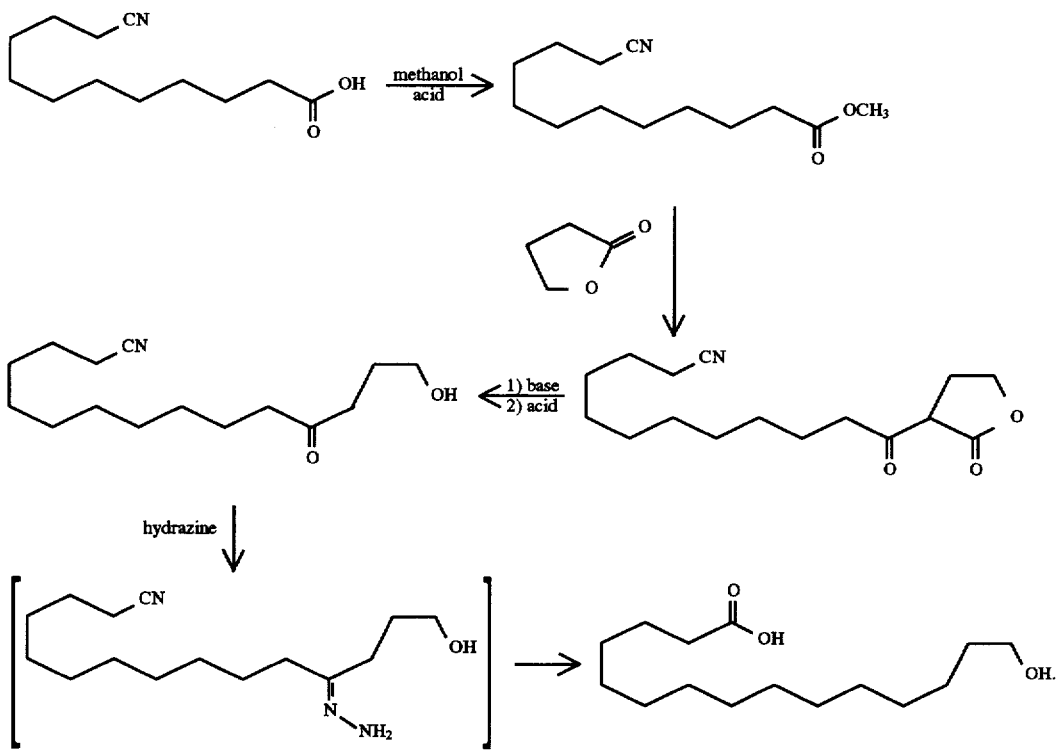

Furthermore, Japanese Published Application No. 03/011036 of Jan. 18, 1991 as well as European Patent No. 402,063 published on Dec. 12, 1990 discloses the reaction sequence:

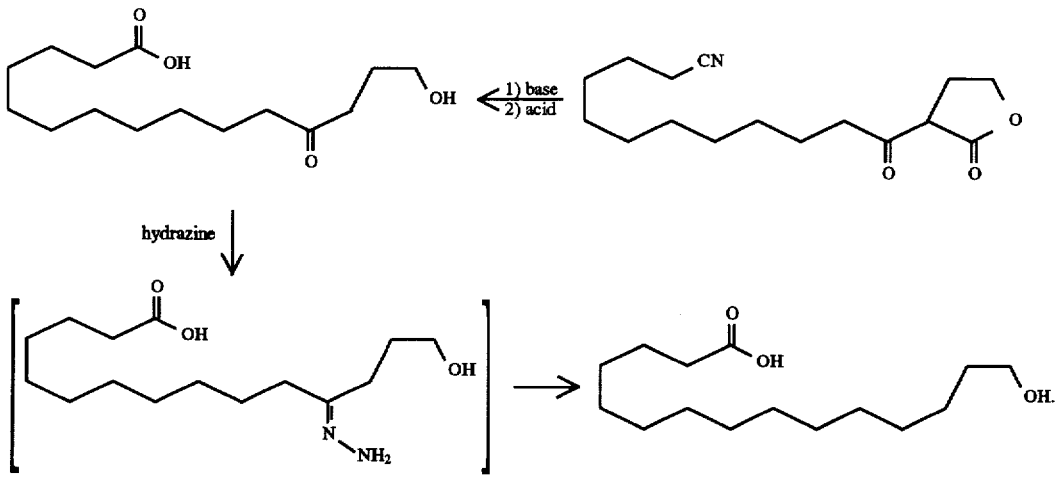

Furthermore, the reaction of a dicarboxylic acid with butyrolactone is known (Staker, Monsanto U.S. Pat. No. 3,014,044 issued on Dec. 19, 1961 . . . substituted succinic acid reacted with butyrolactone to form rust preventative compositions) and the Wolff-Kishner reduction of keto-carboxylic acids is known [Todd, *Organic Reactions*, Chapter 8, Volume 4 (1948), pages 378–422, particularly at page 391; Cason, et al, *J. Org. Chem.*, 1950, Volume 15, pages 850–859; and Bachmann, *J. Am. Chem. Soc.*, 1951, 73, pages 51–54].

Nevertheless, the use and formation of the intermediate having the structure:

is not disclosed or implied in the prior art, and the use of such intermediate having the structure:

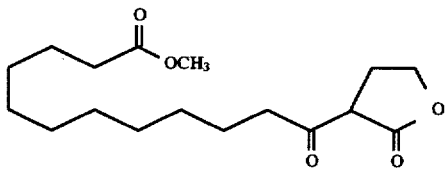

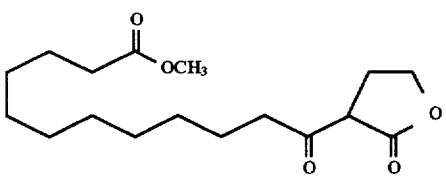

represents an advance in the art to ultimately lead to a much more efficient and low cost cyclopentadecanolide having the structure:

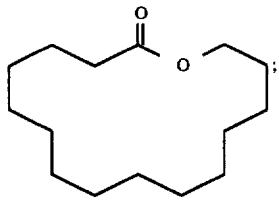

so important in the field of perfumery.

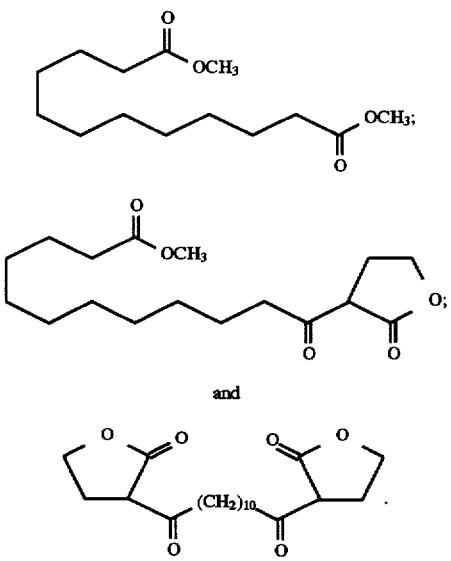

FIG. 2 is the NMR spectrum for the compound having the structure:

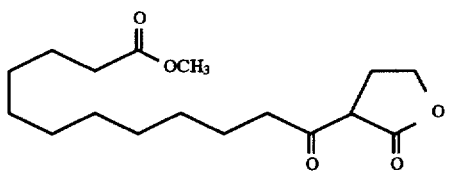

prepared according to Example I.

FIG. 2A is an enlargement of section "A" of the NMR spectrum of FIG. 2.

FIG. 2B is an enlargement of section "B" of the NMR spectrum of FIG. 2.

FIG. 2C is an enlargement of section "C" of the NMR spectrum of FIG. 2.

FIG. 2D is an enlargement of section "D" of the NMR spectrum of FIG. 2.

FIG. 3A is the GC spectrum for the reaction product of Example IV using an OV-1 column, containing the compound having the structure:

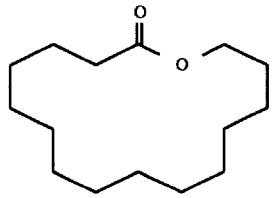

FIG. 3B is a GC spectrum for the reaction product of Example IV using a CARBOWAX® column, containing the compound having the structure:

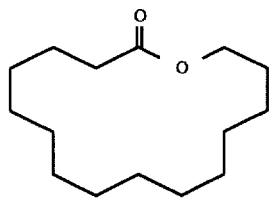

FIG. 4 is the NMR spectrum for the compound having the structure:

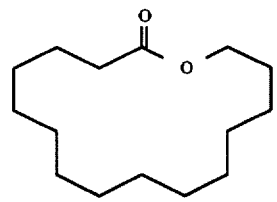

prepared according to Example IV.

Figures 5, 6:
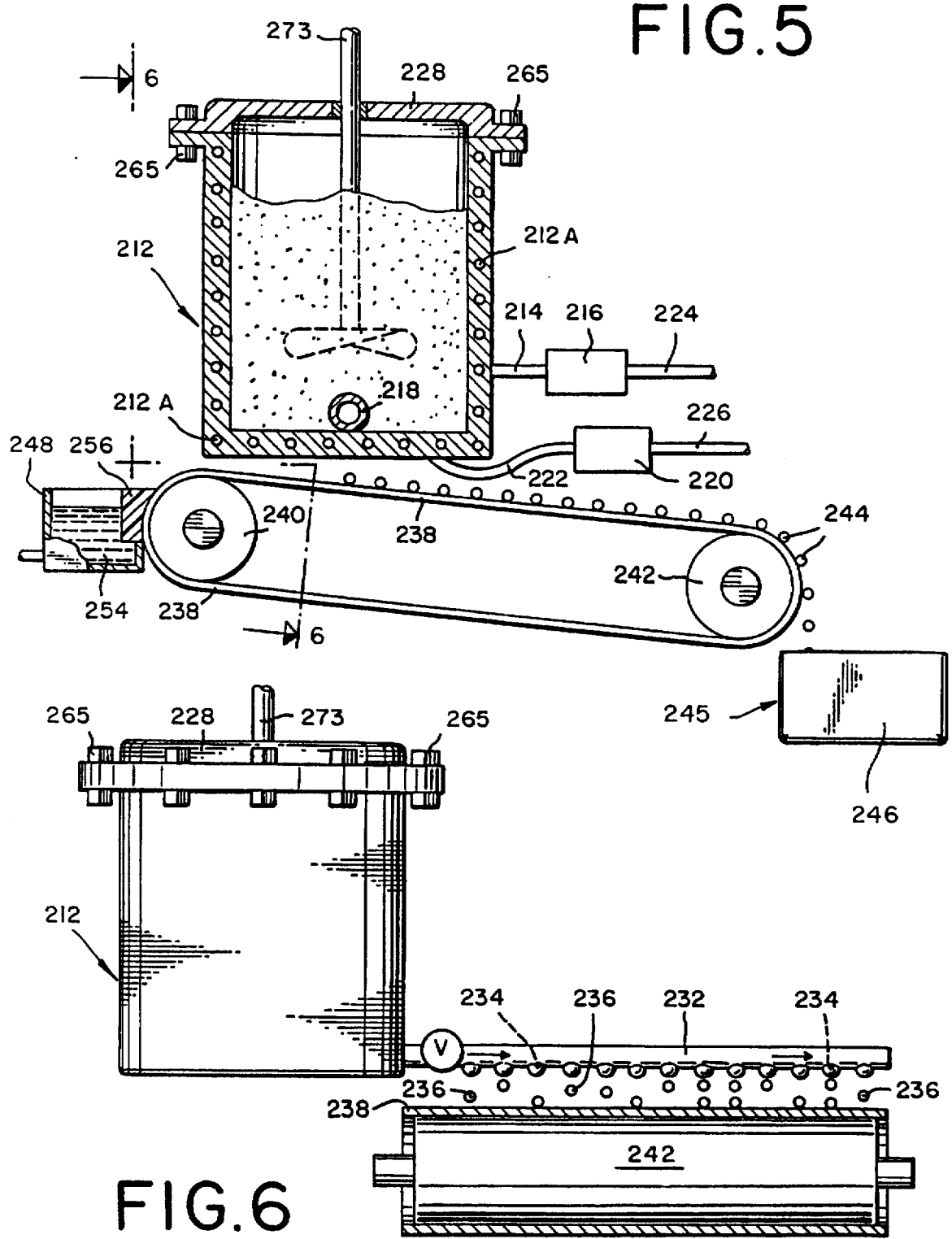

FIG. 5 represents a cutaway side elevation view of apparatus used in forming perfumed polymers which contain embedded in the interstices thereof the cyclopentadecanolide produced according to the process of my invention.

FIG. 6 is a front view of the apparatus of FIG. 5 in the direction of the arrows.

DETAILED DESCRIPTION OF THE DRAWINGS

Figure 1:
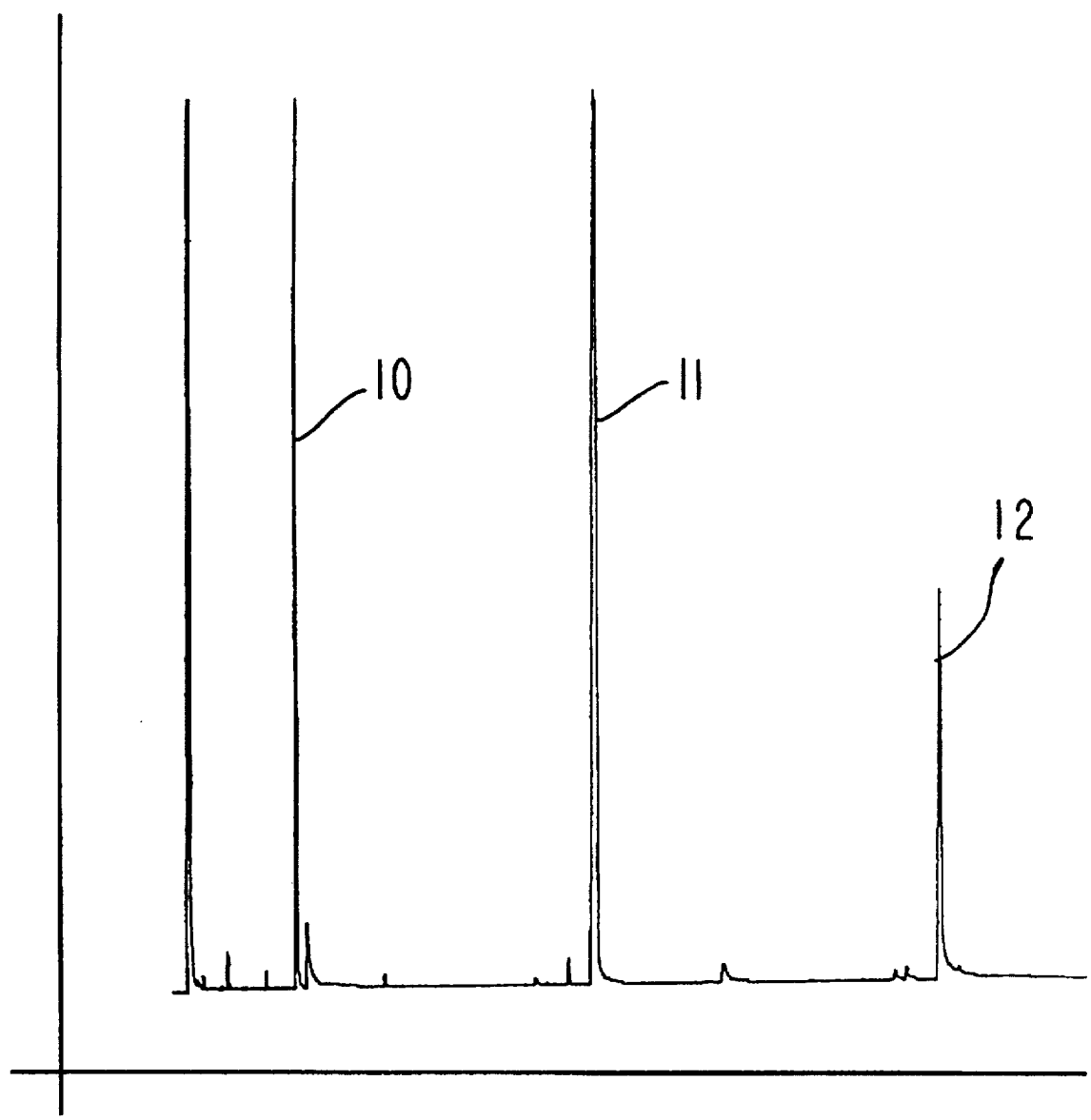
FIG. 1 is the GLC profile for the reaction product of Example I containing the compounds having the structures.

Referring to FIG. 1, FIG. 1 is the GLC profile for the reaction product of Example I (conditions: 30 meter OV-1 column programmed from 170°–280° C. at 4° C. per minute). The peak indicated by reference numeral 10 is the peak for the starting material having the structure:

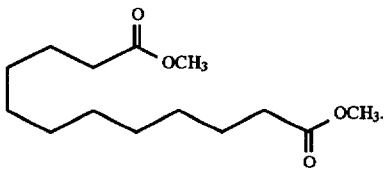

The peak indicated by reference numeral 11 is the peak for the reaction product having the structure:

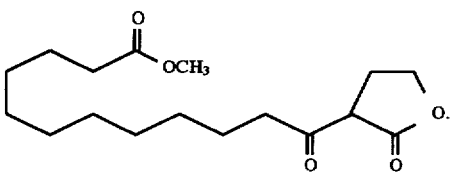

The peak indicated by reference numeral 12 is the peak for the by-product having the structure:

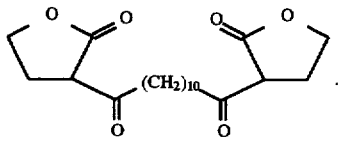

Referring to FIG. 3A, FIG. 3A is a GC spectrum for the reaction product of Example IV. The spectrum is carried out using an OV-1 column. The peak indicated by reference numeral 30 is the peak for the lactone having the structure:

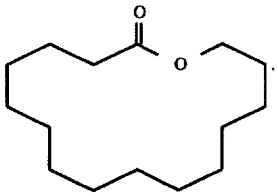

The peak indicated by reference numeral 31 is the peak for the reaction solvent, glycerol.

Referring to FIG. 3B, FIG. 3B is the GC spectrum for the reaction product of Example IV using a CARBOWAX® column. The peak indicated by reference numeral 32 is the peak for the lactone having the structure:

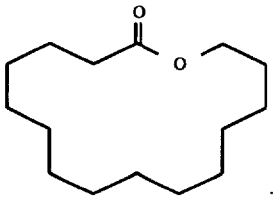

The peak indicated by reference numeral 33 is the peak for the solvent, glycerol.

Referring to FIGS. 5 and 6, there is provided a process for forming scented polymer elements (wherein the polymer may be a thermoplastic polymer such as low density polyethylene or polypropylene or copolymers of ethylene-vinyl acetate or mixtures of a polymer and copolymer such as a copolymer of ethylene-vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower-most portion of the container is maintained at a slightly lower temperature and the material in the container is taken off at such location for delivery through the conduit. Thus, referring to FIGS. 5 and 6, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymers and a perfuming substance containing the cyclopentadecanolide produced according to the process of my invention is placed. The container is closed by means of an air-tight lid 228 and clamped to the container by bolts 265. A stirrer 273 traverses the lid or cover 228 in an air-tight manner and is rotatable in a suitable manner.

A surrounding cylinder 212 having heating coils 212A which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 Sayboldt seconds. The heater is operated to maintain the upper portion of the container 212, within a temperature range of, for example, 250°–270° C. in the case of low density polyethylene. The bottom portion of the container 212 is heated by means of heating coils 212A regulated through the control 220 connected thereto through a connecting wire 222 to maintain the lower portion of the container 212 with a temperature range of 225°–240° C.

Thus, the polymer or mixture of polymers added to the container 212 is heated from 10–12 hours, whereafter the perfume composition or perfume material containing the cyclopentadecanolide produced according to the process of my invention is quickly added to the melt. Generally, about 10–45% by weight of the resulting mixture of perfumery substance is added to the polymer.

After the perfume material is added to the container 212, the mixture is stirred for a few minutes, for example, 5–15 minutes, and maintained within the temperature ranges indicated previously by the heating coils 212A. The controls 216 and 220 are connected through cables 224 and 226 to a suitable supply of electric current for supplying the power for heating purposes.

Thereafter, the valve "V" is opened permitting the mass to flow outwardly through conduit 232 (also indicated by pipe 218) having a multiplicity of orifices 234 adjacent to the lower side thereof. The outer end of the conduit 232 is closed so that the liquid polymer initmately admixed with the cyclopentadecanolide produced according to the process of my invention and other materials, if desired, will continuously drop through the orifices 234 downwardly from the conduit 232. During this time, the temperature of the polymer intimately admixed with the perfumery substance in the container 212 is accurately controlled so that a temperature in the range of from about 240°–250° C. (in the case of low density polyethylene) will exist in the conduit 232. The regulation of the temperature through the controls 216 and 220 is essential in order to insure temperature balance to provide for the continuous dropping or dripping of molten polymer intimately admixed with the perfume substance containing the cyclopentadecanolide produced according to the process of my invention and other materials compatible therewith through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 245 which is advantageously filled with water 246 or some other suitable cooling liquid to insure the rapid cooling of each of the pellets 244. The pellets 244 are then collected from the container 245 and utilized for formation of other functional products, e.g., garbage bags and the like.

The conveyor 238 is premoistened using sponge 256 which rests within container 248 and also impinges upon conveyor belt 238. Water 254 or other cooling liquid is contained in container 248 and the water or other cooling liquid is absorbed into sponge 256 prior to moistening belt 238.

THE INVENTION

My invention relates to the production of cyclopentadecanolide defined according to the structure:

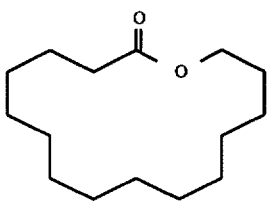

according to the reaction sequence:

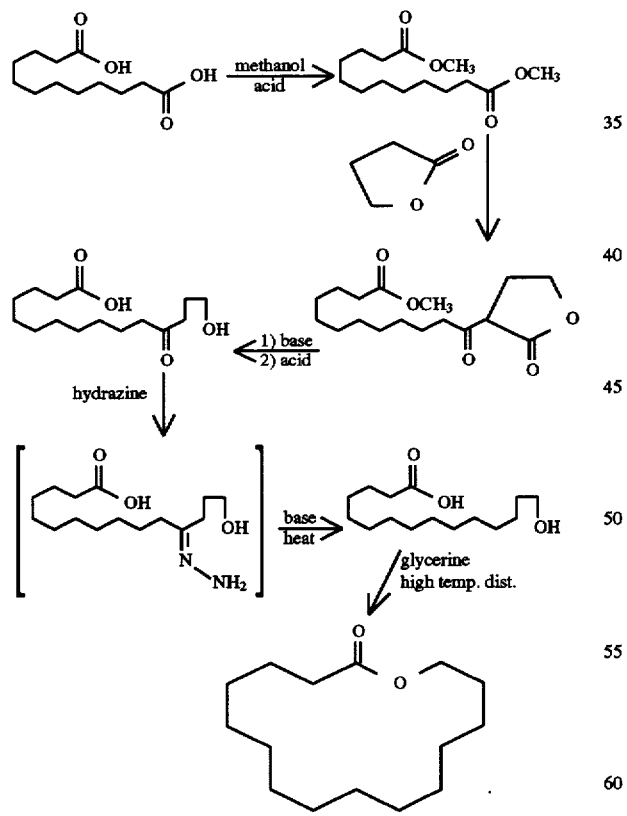

My invention also relates to the additional process step of intimately admixing the resulting cyclopentadecanolide having the structure:

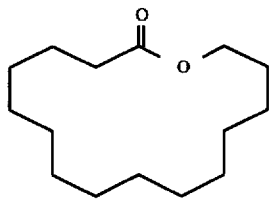

with perfume compositions, perfumed articles or colognes. Examples of such perfumed articles are solid or liquid anionic, cationic, nonionic or zwitterionic detergents, perfumed polymers, fabric softener compositions, fabric softener articles, cosmetic powders and hair preparations.

My invention also relates to mixtures of the cyclopentadecanolides produced according to the process of my invention with other musk chemicals including those defined according to the structures:

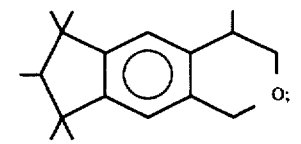

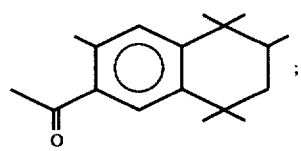

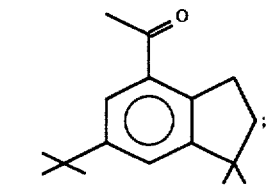

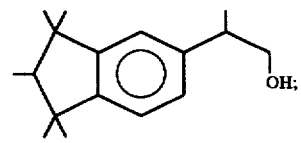

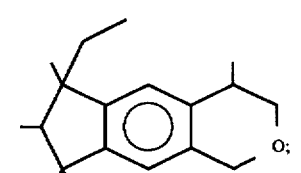

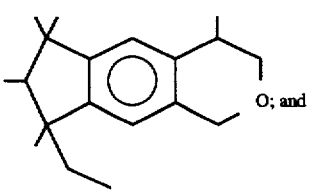

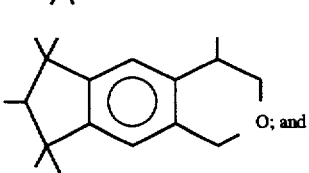

-continued

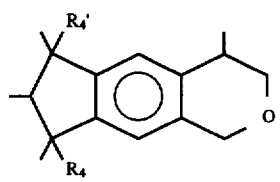

wherein the structure:

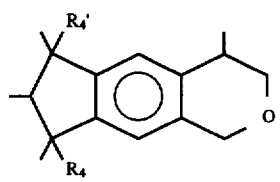

represents a mixture wherein, in the mixture in one of the compounds, $R_4$ and $R_4'$ are both methyl (about 90% of the mixture by weight); and in the other compounds, one of $R_4$ or $R_4'$ is methyl and the other of $R_4$ or $R_4'$ is ethyl (about 10% by weight of the compounds).

With respect to the reaction sequence, to wit:

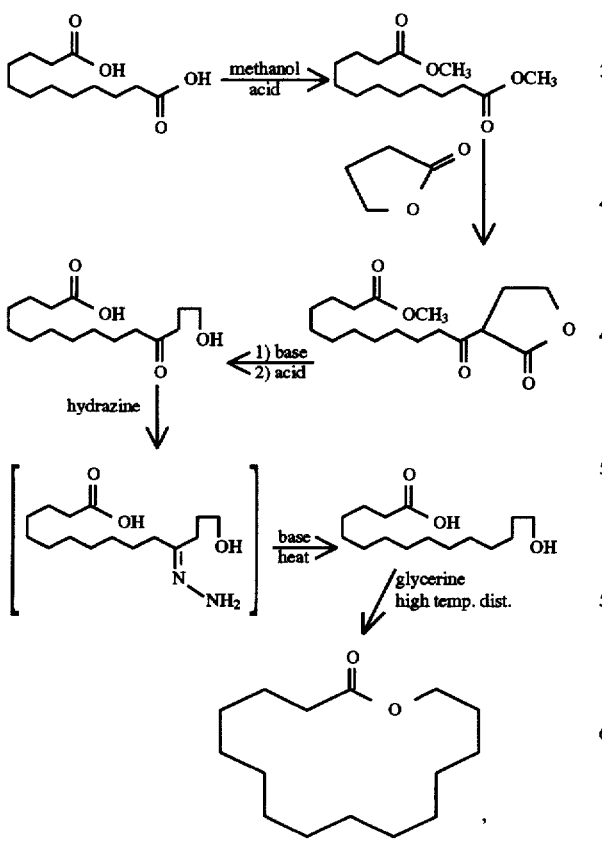

the known dicarboxylic acid having the structure:

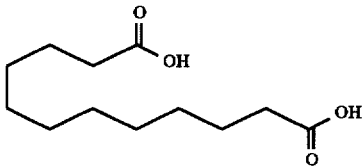

is esterified to form the methyl ester using standard prior art esterification techniques, for example, the reaction thereof with methyl alcohol in the presence of a sulfuric acid catalyst to form the compound having the structure:

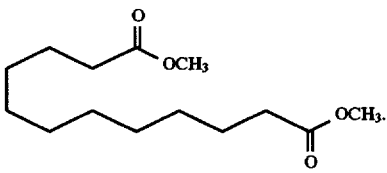

With respect to the reaction:

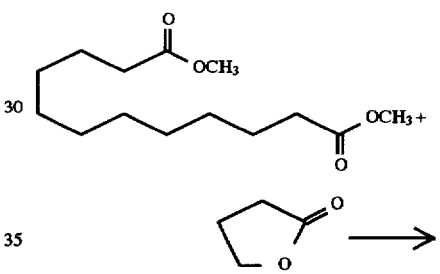

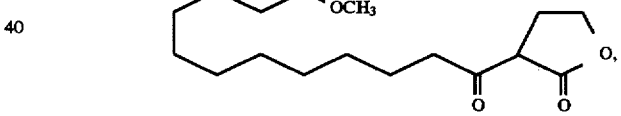

the reaction is carried out in the presence of an alkali metal alkoxide such as sodium methylate in the presence of a non-reactive solvent which is a lower alkanol such as methyl alcohol. Potassium-t-butoxide can be used in place of the sodium methylate. Preferably, the alkali metal alkoxide useful is 25% sodium methylate in methanol. The reaction temperature may vary between about 80° C. and about 130° C. with 110° C. preferred. Other esters besides methyl ester having the structure:

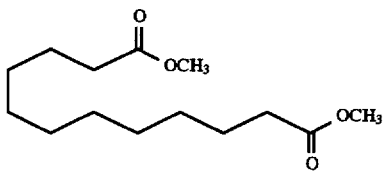

can be used, for example, the ethyl ester. The mole ratio of the butyrolactone having the structure:

13

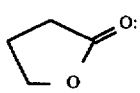

the ester having the structure:

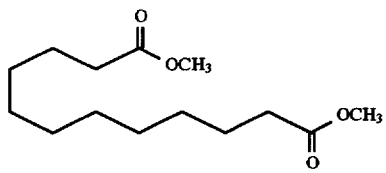

(or ethyl ester) may vary from about 1:1 up to about 1:4.

At the end of the reaction, the reaction mass is cooled and admixed with a dilute base such as dilute sodium hydroxide and then extracted with an inert solvent such as methylene dichloride. The resulting product having the structure:

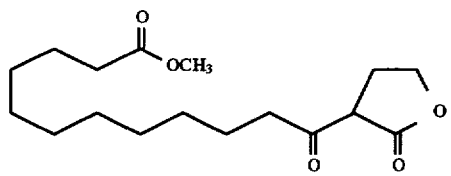

is a crystal. The GLC profile is set forth in FIG. 1. The NMR analysis of the compound having the structure:

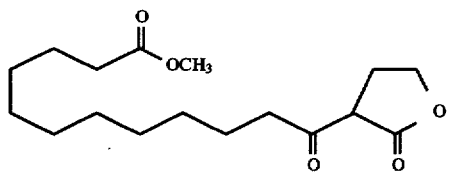

is set forth in FIGS. 2, 2A, 2B, 2C and 2D. The compound having the structure:

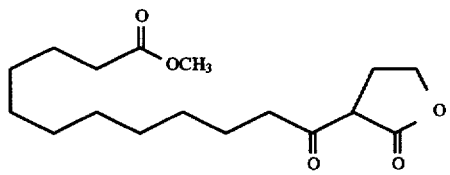

is unknown in the prior art.

With respect to the reaction:

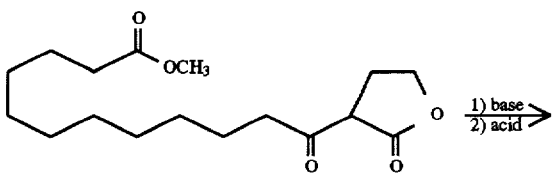

14

-continued

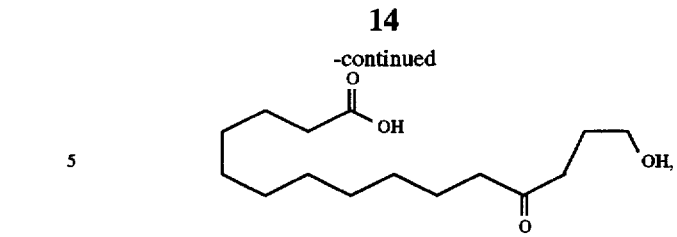

the reaction goes through two steps, firstly, a decyclization step using base such as sodium hydroxide (from 10 up to about 50% aqueous sodium hydroxide); or in place of the sodium hydroxide, potassium hydroxide can be used. The second step is a decarboxylation using acid.

The reaction is carried out in the presence of a solvent such as ethyl alcohol, dioxane or tetrahydrofuran; or the reaction can take place in the absence of such solvent. The reaction is exemplified in Example II, infra.

With respect to the reaction:

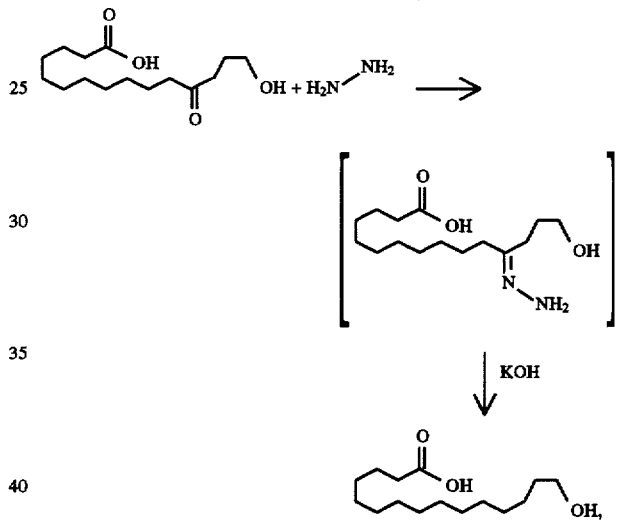

this reaction takes place using 80% hydrazine hydrate in aqueous solution, or the hydrazine can be used as is or the hydrazine hydrate can be used as is. The reaction takes place using solid base such as potassium hydroxide flakes and a nonreactive solvent, for example, diethylene glycol whereby the reaction mass can be heated to the reaction temperature which is about 200° C.

At the end of the initial reaction forming the hydrazone derivative having the structure:

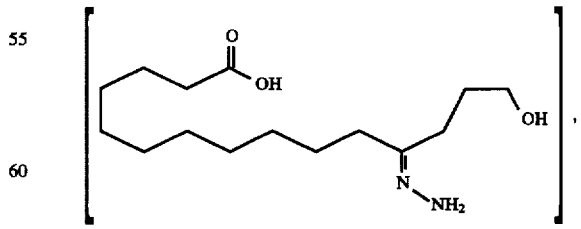

the hydrazone derivative is then treated with mineral acid such as concentrated hydrochloric acid (that is, concentrated 85% aqueous hydrochloric acid) whereby the resulting product having the structure:

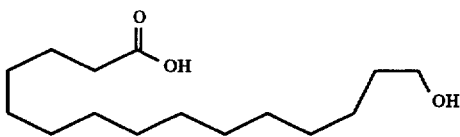

is formed.

With respect to the reaction:

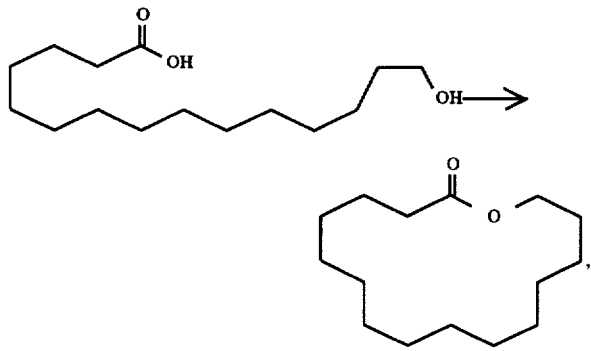

this reaction takes place in the presence of a base such as potassium carbonate and a glycerol solvent. The weight ratio of glycerol:the compound having the structure:

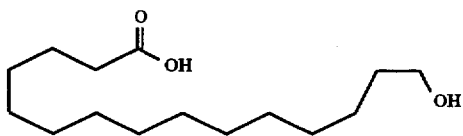

is preferably about 3:1 (mole ratio, 7:1). The amount of base, that is potassium carbonate preferably, in the reaction mass is 8 grams per 1,000 grams of reactant mixture.

The reaction takes place at a temperature in the range of from about 180° C. up to about 220° C. and a pressure in the range of from 15 up to about 30 mm/Hg. As the reaction proceeds, the reaction product and solvent are co-distilled with the glycerol solvent being returned to the reaction vessel and the reaction product having the structure:

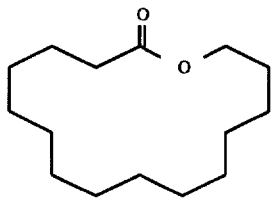

being collected.

The time of reaction may vary from about 6 hours up to about 10 hours. This reaction is exemplified in Example IV, infra.

The cyclopentadecanolide having the structure:

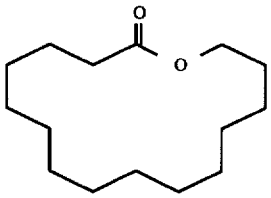

prepared according the process of my invention has an animal, musky and sweet aroma profile. With respect to flavors, the cyclopentadecanolide of our invention having the structure:

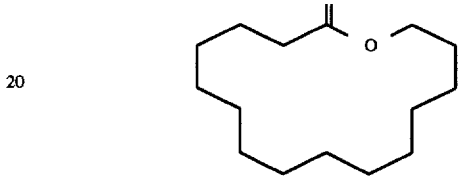

is useful in berry flavors, liquor, wine, brandy, fruit, nut and vanilla-containing compositions.

The cyclopentadecanolide produced according to the process of my invention and, if desired, one or more additional musk chemicals as set forth, supra, and, if desired, one or more auxiliary perfume ingredients including, for example, hydrocarbons, alcohols, ketones, aldehydes, nitriles, esters, lactones (other than the lactone produced according to the process of my invention), ethers, hydrocarbons, chlorinated derivatives, synthetic essential oils and natural essential oils may be admixed so that the combined odors of the individual components produce a pleasant and desired fragrance particularly and preferably in the musk fragrance area. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics; however, the overall sensory effect of the perfume composition will be at least the sum total of the effects of each of the ingredients. Thus, the cyclopentadecanolide produced according to the process of my invention taken alone or taken further together with at least one musk chemical such as the compound having the structure:

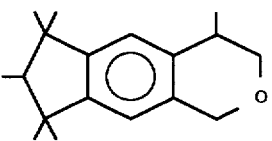

can be used to alter, modify or enhance the aroma characteristics of a perfume composition, for example, by utilizing or moderating the olfactory reaction contributed by another ingredient in the composition.

The amount of the cyclopentadecanolide produced according to the process of my invention which will be effective in perfume compositions as well as in perfumed articles and colognes depends upon many factors, including the other ingredients (e.g., other musk chemicals such as the compounds having the structures:

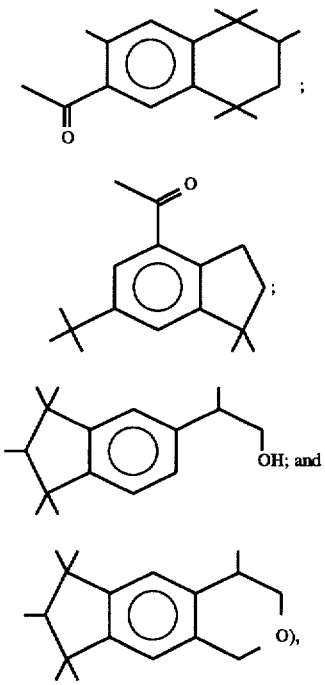

their amounts and the effects which are desired. It has been found that perfume compositions containing as little as 0.005% of cyclopentadecanolide produced according to the process of my invention or even less (e.g., 0.002%) can be used to impart an intense, long-lasting and substantive animal, musky and sweet aroma to soaps, cosmetics, detergents (including anionic, cationic, nonionic or zwitterionic solid or liquid detergents) or other products. The amount employed can range up to 100% of the fragrance components and will depend upon considerations of cost, nature of the end product, the effect desired on the finished product and the particular fragrance sought.

The cyclopentadecanolide produced according to the process of my invention taken alone or further together with other musk chemicals including the compounds having the structures:

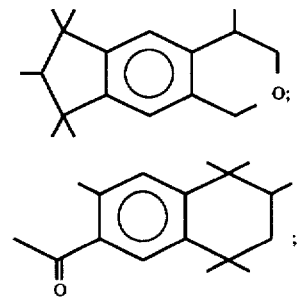

-continued

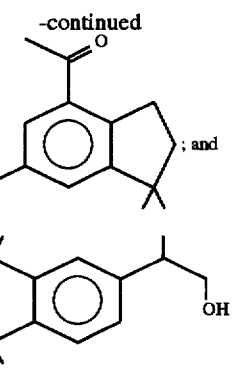

are useful (taken alone or together with other ingredients in perfume compositions) in detergents and soaps; space odorants and deodorants; perfumes; colognes; toilet water; bath preparations such as lacquers, brilliantines, pomades and shampoos; cosmetic preparations such as creams, deodorants, hand lotions and sun screens; powders such as talcs, dusting powders, face powders and the like.

As little as 0.7% of the cyclopentadecanolide produced according to the process of my invention will suffice to impart an intense and substantive natural animalic, sweet, musky aroma to musk perfume formulations. Generally, no more than 5% of the cyclopentadecanolide produced according to the process of my invention based on the ultimate end product is required to be used "as is" or in the perfume composition.

Furthermore, as little as 0.25% of the cyclopentadecanolide produced according to the process of my invention taken alone or taken further together with at least one more musk chemical such as the compound having the structure:

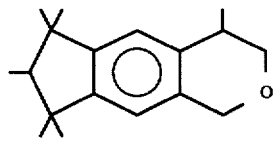

will suffice to impart such aroma to perfumed articles per se, whether in the presence of other perfume materials or whether used by itself. Thus, the range of use of cyclopentadecanolide produced according to the process of my invention in perfumed articles may vary from about 0.25% up to about 5% by weight based on the total weight of the perfumed article.

In addition, the perfume composition or fragrance composition of my invention can contain a vehicle or carrier for the cyclopentadecanolide produced according to the process of my invention taken alone or taken together with at least one other musk chemical such as the compound having the structure:

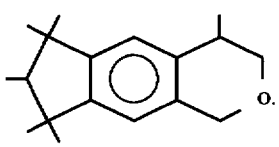

The vehicle can be a liquid such as a non-toxic alcohol, e.g., ethanol; a non-toxic glycol, e.g., propylene glycol or the like. The carrier can also be an absorbent solid such as a gum (e.g., gum arabic) or components for encapsulating the composition by means of a coacervation (such as gelatin).

It will thus be apparent that the cyclopentadecanolide produced according to the process of my invention taken alone or taken together with another musk chemical such as a musk chemical having one of the structures:

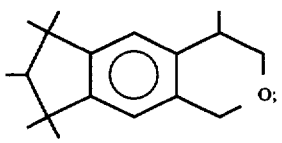

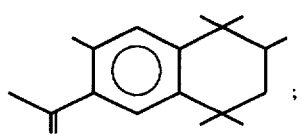

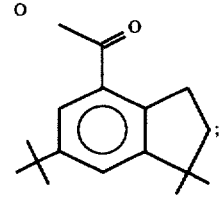

and/or

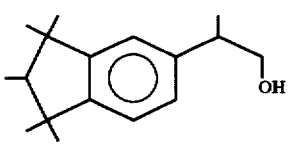

can be utilized to alter, modify or enhance the aroma of perfume compositions, colognes or perfumed articles.

The following Examples I, II, III and IV serve to illustrate processes for producing the cyclopentadecanolide of my invention. Examples following Example IV, in general, serve to illustrate organoleptic utilities of the cyclopentadecanolide produced according to the process of my invention.

In general, the following examples serve to illustrate specific embodiments of my invention. It will be understood that these examples are illustrative and that the invention is to be considered restricted thereto only as indicated in the appended claims.

All parts and percentages given herewith are by weight unless otherwise specified.

EXAMPLE I

Preparation of Ω-Carbomethoxy Undecanoyl Butyrolactone

Reaction:

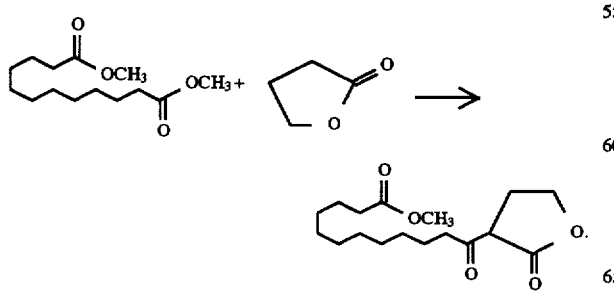

Materials:

| | |
|---|---|
| dimethyl cyclododecanoate | 920 grams (4 moles); |
| 25% sodium methylate in methanol | 432 grams (2 moles); |
| γ-butyrolactone | 172 grams (2 moles); |
| 5% aqueous sodium hydroxide | 1,000 mls; |
| CH$_2$Cl$_2$ (methylene dichloride) | 800 mls; and |
| concentrated aqeous HCl | 330 mls. |

Procedure:

Charge the dimethyl ester, butyrolactone and 25% sodium methylate solution to a 3 liter flask. Heat to 110° C. with stirring while distilling off methanol to a pot temperature of 110° C. Stir at 110° C. for 2 hours. Cool to 25° C. Add 1 liter water, then 1 liter of 5% aqueous sodium hydroxide. Extract once with 400 mls of methylene dichloride; then two times with 200 ml methylene dichloride to remove unreacted dimethyl dodecanoate. With stirring and cooling, feed 330 mls of concentrated aqueous hydrochloric acid to the stirred aqueous solution. The resulting crystals are washed with water and air-dried to afford 483 grams of ω-carbomethoxy undecanoyl butyrolactone (83% of theory).

FIG. 1 is the GLC profile of the reaction product. The peak indicated by reference numeral 10 is the peak for the starting material having the structure:

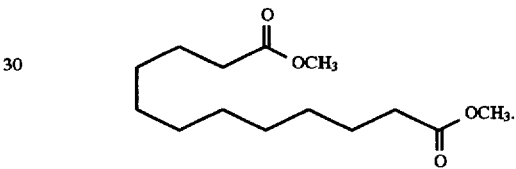

The peak indicated by reference numeral 11 is the peak for the reaction product having the structure:

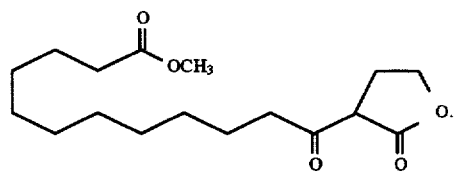

The peak indicated by reference numeral 12 is the peak for the side product having the structure:

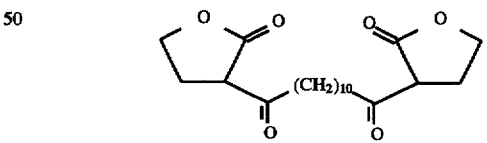

FIG. 2 is the NMR spectrum for the compound having the structure:

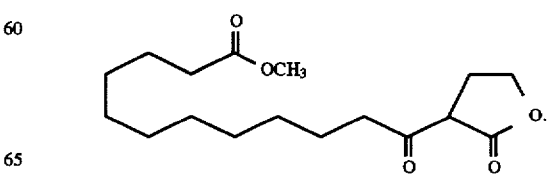

EXAMPLE II

Preparation of 15-Hydroxy-4-Ketododecanoic Acid

Reaction:

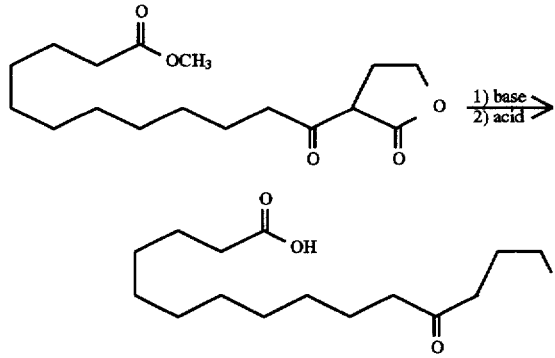

450 Grams (1.5 moles) of the material produced in Example I having the structure:

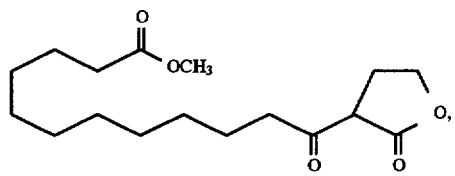

800 mls of 20% aqueous sodium hydroxide and 300 grams of methanol are admixed and heated to reflux and maintained at reflux for a period of 3 hours. The resulting solution is cooled to 40° C. 10% Aqueous hydrochloric acid (1,300 mls) is added to the reaction mass over a 1 hour period while carbon dioxide gas is being released from the reaction mass. Crystals are precipitated. The resulting crystals are washed with water and collected by filtration. The resulting crystals are then washed with water and air-dried to afford 365 grams of 15-hydroxy-4-ketododecanoic acid (90% of theory) having the structure:

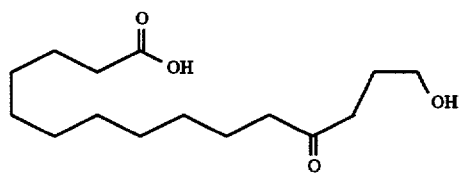

as confirmed by NMR, IR and mass spectral analyses.

EXAMPLE III

Preparation of 15-Hydroxypentanoic Acid

Reaction:

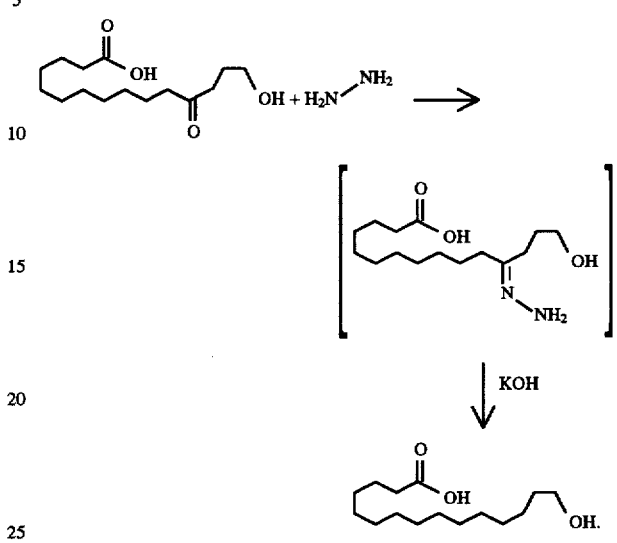

A stirred suspension of 15-hyroxy-4-ketododecanoic acid prepared according to Example II having the structure:

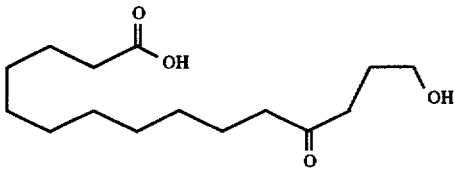

(365 grams, 1.35 moles), 80% hydrazine hydrate (aqueous solution) (102 grams, 1.6 moles), 85% potassium hydroxide flakes (263 grams, 4 moles) and diethylene glycol was heated to 110° C. for 1 hour. The resulting solution was slowly heated then to 200° C. over a 2 hour period while distilling out the water and releasing the nitrogen.

The resulting solution was then stirred at 200° C. for another 2 hour period, then cooled to 80° C. The hot solution was then poured onto 1,400 mls of water while stirring. The resulting solution is now at a temperature of 40° C. At 40° C., a 15% aqueous hydrochloric acid solution (1,000 grams) was added with stirring and cooling. The deposited crystals were washed thoroughly with water and air-dried to afford 318 grams of 15-hydroxypentadecanoic acid having the structure:

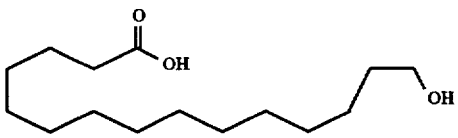

as confirmed by NMR, IR and mass spectral analyses.

EXAMPLE IV

Preparation of Cyclopentadecanolide from 15-Hydroxypentadecanoic Acid

Reaction:

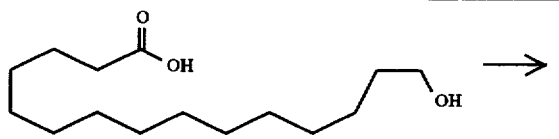

→

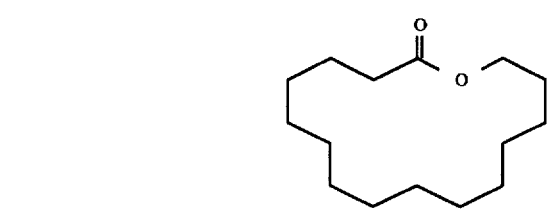

| Reagents | Amount (Grams) | Gram Moles |
|---|---|---|
| 15-hydroxypentadecanoic acid | 500 | 1.95 |
| glycerol | 1,500 | 13.5 |
| potassium carbonate | 25 | 0.18 |

Apparatus:

3 Liter, three-neck glass reaction flask equipped with a mechanical stirrer, stir shaft, bearing, Teflon blade, "modified" Bidwell trap, condenser with tempered water, vacuum pump, thermometer, heating mantle and Therm-o-watch.

[Note: The Bidwell trap was modified to allow a steady return of the lower distillate layers (predominantly glycerol) back to the reaction flask.]

Procedure:

The modified Bidwell trap is charged with 500 grams of glycerol. The reaction flask is charged with glycerol (1,000 grams), 15-hydroxypentadecanoic acid (500 grams) and potassium carbonate (25 grams). The condenser water is set at 60° C. The reaction mixture is stirred and heated to 120° C. The pressure is lowered to 20 mm/Hg vacuum. Heating is continued and the reaction begins to reflux at a pot temperature of 191° C. The distillate mixture of cyclopentadecanolide having the structure:

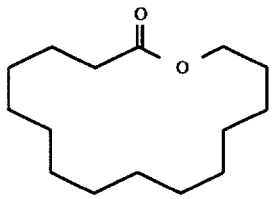

and glycerol is collected. It separates into two layers in the moisture trap. The cyclopentadecanolide layer is on top (the Bidwell trap is surrounded by heat tape to avoid the solidification of the cyclopentadecanolide). The bottom glycerol layer is slowly returned to the pot. A stopcock is adjusted so that the return flow keeps the pot level steady. The distillate is collected for a period of 8 hours with a pot temperature ranging from 191°–215° C.

Results:

A total of 355 grams of cyclopentadecanolide was collected. This represents a 76% chemical yield. The synthesized cyclopentadecanolide having the structure:

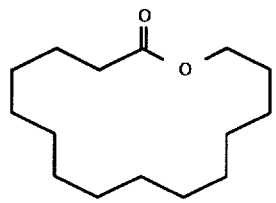

was confirmed by NMR and Capillary GC IE values.

The distillation fractions collected are as follows:

| Fraction Number | Vapor Temperature (°C.) | Liquid Temperature (°C.) | Reflux Ratio | Vacuum mm/Hg. Pressure | Weight of Fraction |
|---|---|---|---|---|---|
| 1 | 48 | 110 | 100 | 1.8 | 8 |
| 2 | 151 | 170 | 9/1 | 1.8 | 12 |
| 3 | 145 | 168 | 9/1 | 1.8 | 18 |
| 4 | 145 | 169 | 1/1 | 1.8 | 18 |
| 5 | 145 | 169 | 1/1 | 1.7 | 20 |
| 6 | 149 | 169 | 1/1 | 1.75 | 23 |
| 7 | 150 | 169 | 1/1 | 1.75 | 23 |
| 8 | 149 | 170 | 1/1 | 1.75 | 26 |
| 9 | 149 | 171 | 1/1 | 1.75 | 27 |
| 10 | 150 | 173 | 1/1 | 1.75 | 28 |
| 11 | 150 | 173 | 1/1 | 1.75 | 28 |
| 12 | 150 | 174 | 1/1 | 1.75 | 32 |
| 13 | 150 | 175 | 1/1 | 1.75 | 22 |
| 14 | 148 | 181 | 1/1 | 1.75 | 28 |
| 15 | 143 | 188 | 1/1 | 1.7 | 23 |
| 16 | 143 | 198 | 1/1 | 1.6 | 10 |

FIGS. 3A and 3B are GC spectra for the reaction product prior to distillation. FIG. 3A is the GC spectrum using an OV-1 column. The peak indicated by reference numeral 30 is the peak for the compound having the structure:

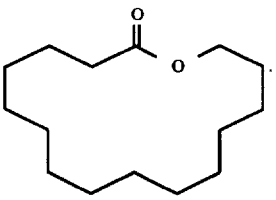

The peak indicated by reference numeral 31 is the peak for the reaction solvent, glycerin.

FIG. 3B is the GC spectrum for the reaction product using a CARBOWAX® column. The peak indicated by reference numeral 32 is the peak for the reaction product having the structure:

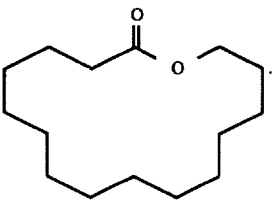

The peak indicated by reference numeral 33 is the peak for the solvent, glycerol. FIG. 4 is the NMR spectrum for the cyclopentadecanolide having the structure:

The cyclopentadecanolide having the structure:

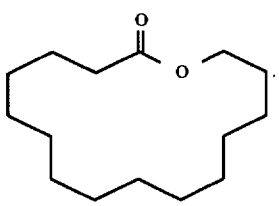

bulked distillation fractions 6–13 has an intense and substantive animalic, sweet, musky aroma profile.

EXAMPLE V

Musk Perfume

The following musk perfume is prepared:

| Ingredient | Parts by Weight |
| --- | --- |
| The compound having the structure: 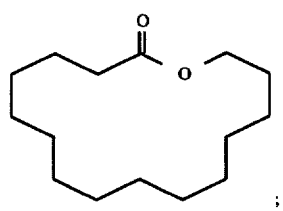 | 64 |
| The compound having the structure: 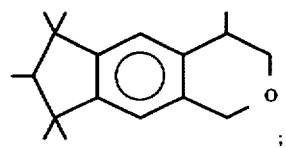 | 32 |
| The compound having the structure: 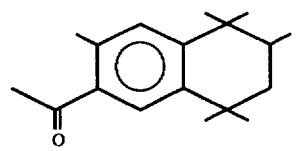 | 16 |
| The compound having the structure: 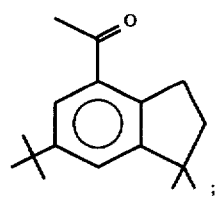 | 16 |
| The compound having the structure: 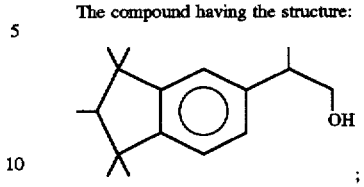 | 20 |
| The mixture of compounds defined according to the structure: 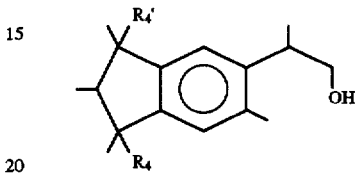 (wherein the structure represents a mixture wherein in the mixture in one of the compounds $R_4$ and $R_4'$ are both methyl; and in the other compounds, one of $R_4$ or $R_4'$ is methyl and the other is ethyl); | 20 |
| The mixture of compounds having the structure: 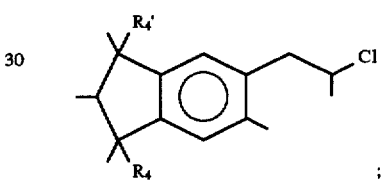; and | 20 |
| The mixture of compounds having the structure: 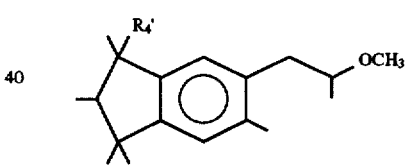 | 20 |

The cyclopentadecanolide produced according to the process of my invention imparts to this musk formulation a natural and intense, sweet animalic undertone. Accordingly, the resulting perfume composition of Example IV can be described as "musky with sweet animalic undertones".

EXAMPLE VI

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below.

TABLE I

| Ingredients | Aroma Description |
| --- | --- |
| The cyclopentadecanolide defined according to the | An intense, natural animalic, sweet, musky aroma. |

TABLE I-continued

| Ingredients | Aroma Description |
| --- | --- |
| structure: | |
| 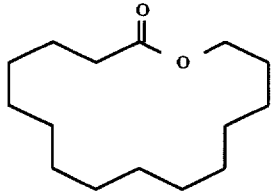 | |
| prepared according to Example IV, bulked distillation fractions 6–13. | |
| Perfume composition of Example V. | A musk aroma with sweet, animalic undertones. |

EXAMPLE VII

Perfumed Liquid Detergents

Concentrated liquid detergents (lysine salt of n-dodecylbenzene sulfonic acid as more specifically described in U.S. Pat. No. 3,948,818 issued Apr. 6, 1976,) with aroma nuances as set forth in Table I of Example VI are prepared containing 0.10%, 0.15%, 0.20%, 0.25%, 0.30% and 0.35% of the substance set forth in Table I of Example VI. They are prepared by adding and homogeneously mixing the appropriate quantity of substance set forth in Table I of Example VI in the liquid detergent. The detergents all possess excellent aromas as set forth in Table I of Example VI, the intensity increasing with greater concentrations of substance as set forth in Table I of Example VI.

EXAMPLE VIII

Preparation of Colognes and Handkerchief Perfumes

Compositions as set forth in Table I of Example VI, are incorporated into colognes at concentrations 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definite fragrances as set forth in Table I of Example VI are imparted to the colognes and to the handkerchief perfumes at all levels indicated.

EXAMPLE IX

Preparation of Soap Compositions

100 Grams of soap chips (per sample) (IVORY® produced by the Procter & Gamble Company of Cincinnati, Ohio) are each mixed with 1 gram samples of substances as set forth in Table I of Example VI until homogeneous compositions are obtained. In each of the cases, the homogeneous compositions are heated under 8 atmospheres pressure at 180° C. for a period of 3 hours and the resulting liquids are placed into soap molds. The resulting soap cakes, on cooling, manifest aromas as set forth in Table I of Example VI.

EXAMPLE X

Preparation of Solid Detergent Compositions

Detergents are prepared using the following ingredients according to Example I of Canadian Patent No. 1,007,948:

| Ingredient | Parts by Weight |
| --- | --- |
| NEODOL ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example VI. Each of the detergent samples has an excellent aroma as indicated in Table I of Example VI.

EXAMPLE XI

Utilizing the procedure of Example I of column 15 of U.S. Pat. No. 3,632,396, non-woven cloth substrates useful as drier-added fabric softening articles of manufacture are prepared wherein the substrate, the substrate coating, the outer coating and the perfuming material are as follows:

1. a water "dissolvable" paper ("Dissolvo Paper");
2. Adogert 448 (m.p. about 140° F.) as the substrate coating; and
3. an outer coating having the following formulation (m.p. about 150° F.):
   58% $C_{20-22}$ HAPS;
   22% isopropyl alcohol;
   20% antistatic agent; and
   1% of one of the perfume materials as set forth in Table I of Example VI.

Fabric softening compositions prepared according to Example I at column 15 of U.S. Pat. No. 3,632,396 having aroma characteristics as set forth in Table I of Example VI, consist of a substrate coating having a weight of about 3 grams per 100 square inches of substrate; a first coating on the substrate coating consisting of about 1.85 grams per 100 square inches of substrate; and an outer coating coated on the first coating consisting of about 1.4 grams per 100 square inches of substrate. One of the substances of Table I of Example VI is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener, non-woven fabrics and these aroma characteristics are described in Table I of Example VI.

EXAMPLE XII

Hair Spray Formulations

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 Grams of the polymer is dissolved in the alcohol. The following ingredients are added to the PVP/VA alcoholic solution:

| Ingredient | Weight Percent |
| --- | --- |
| Dioctyl sebacate | 0.05 |
| Benzyl alcohol | 0.10 |

| Ingredient | Weight Percent |
| --- | --- |
| Dow Corning 473 fluid (prepared by the Dow Corning Corporation) | 0.10 |
| TWEEN ® 20 surfactant (prepared by ICI America Corporation) | 0.03 |
| One of the perfumery substances as set forth in Table I of Example VI | 0.10 |

The perfuming substances as set forth in Table I of Example VI add aroma characteristics as set forth in Table I of Example VI which are rather intense and aesthetically pleasing to the users of the soft-feel, good-hold pump hair sprays.

EXAMPLE XIII

Conditioning Shampoos

A Monamid CMA (prepared by the Mona Industries Company) (3.0 weight percent) is melted with 2.0 weight percent coconut fatty acid (prepared by the Procter & Gamble Company of Cincinnati, Ohio); 1.0 weight percent ethylene glycol distearate (prepared by the Armak Corporation) and triethanolamine (a product of the Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.).

GAFQUAT® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by the Armak Corporation.

The resulting material is then mixed and cooled to 45° C. and 0.3 weight percent of perfuming substance as set forth in Table I of Example VI is added to the the mixture. The resulting mixture is cooled to 40° C. and blending is carried out for an additional 1 hour in each case. At the end of this blending period, the resulting material has a pleasant fragrance as indicated in Table I of Example VI.

What is claimed is:

1. The compound defined according to struture:

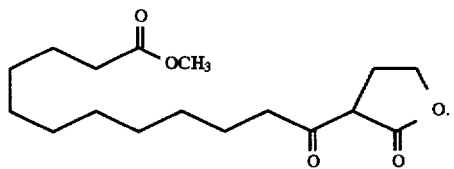

2. A process for preparing the compound having the structure:

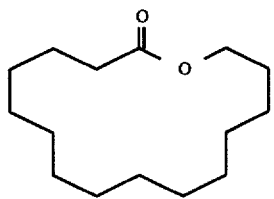

comprising the steps of:

(1) carrying out the reaction:

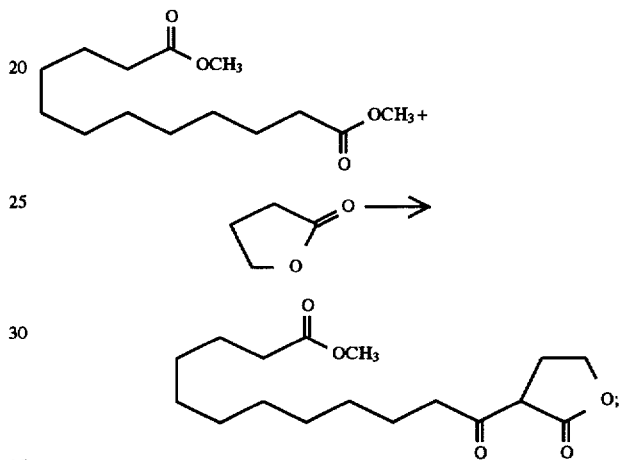

(2) carrying out the reaction:

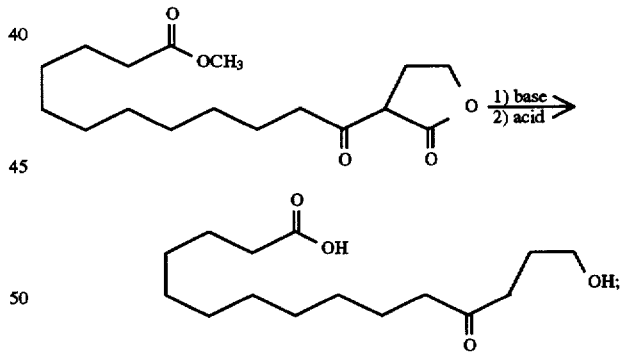

(3) carrying out the reaction:

31

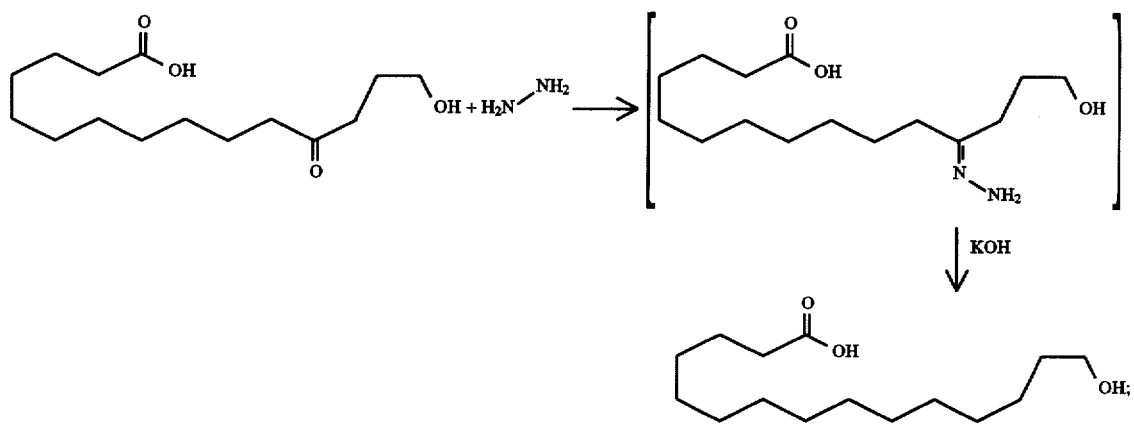

↓ KOH (4) carrying out the reaction:

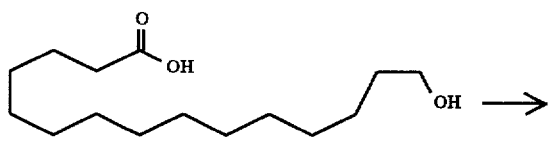

→

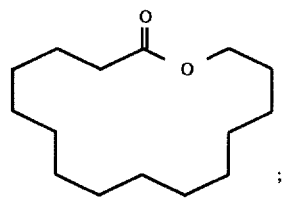

; and (5) fractionally distilling the product having the structure:

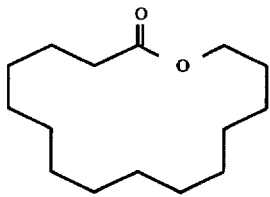

from the reaction mass.

3. The process of claim 2 wherein the reaction:

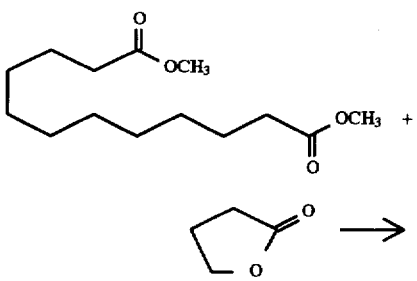

32

-continued

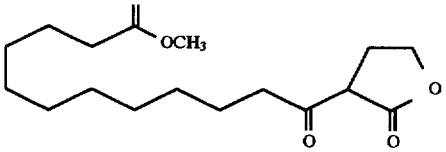

is carried out in the presence of an alkali metal alkoxide; the temperature of reaction is in the range of from about 80° C. up to about 130° C.; and the mole ratio of butyrolactone: the compound having the structure:

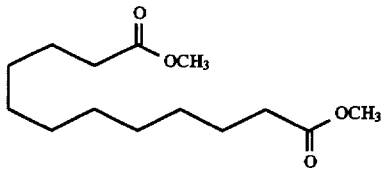

is from about 1:1 up to about 1:4.

4. The process of claim 2 wherein the reaction:

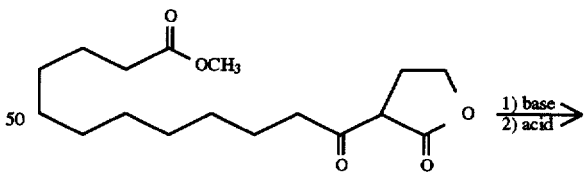

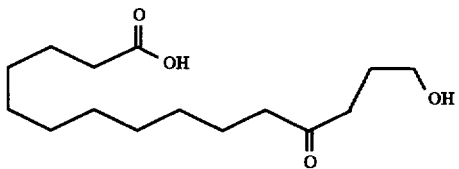

is carried out in the presence of a co-solvent which is selected from the group consisting of an alcohol, dioxane and tetrahydrofuran; and the reaction is carried out in the presence of an aqueous alkali metal hydroxide having a concentration of from about 10% up to about 50% alkali metal hydroxide.

5. The process of claim 2 wherein the reaction:

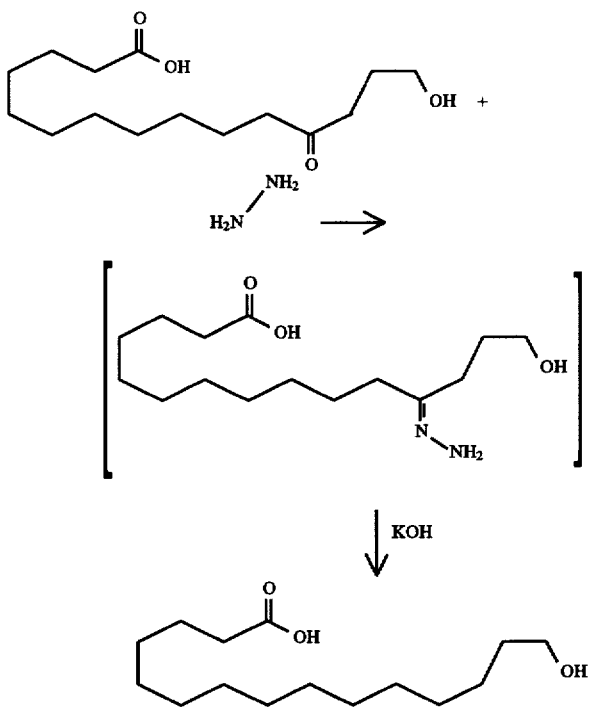

is carried out in the presence of diethylene glycol at a temperature of 200° C.

6. The process of claim 2 wherein the reaction:

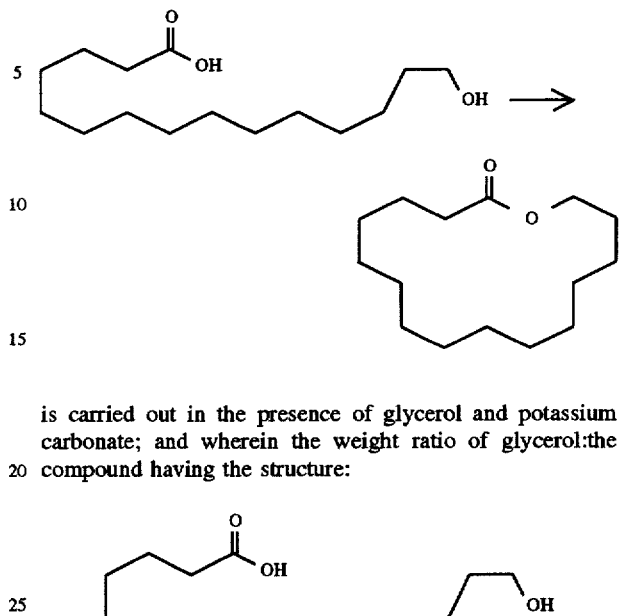

is carried out in the presence of glycerol and potassium carbonate; and wherein the weight ratio of glycerol:the compound having the structure:

is about 3:1 and the weight percent of potassium carbonate in the reaction mass is from about 1% up to about 2%.

* * * * *